United States Patent [19]

Gross et al.

[11] Patent Number: 4,719,930

[45] Date of Patent: Jan. 19, 1988

[54] HAIR TREATMENT AND PROCESS FOR HAIR TREATMENT

[75] Inventors: Paul Gross, Darmstadt; Walter Keller, Ober-Ramstadt, both of Fed. Rep. of Germany

[73] Assignee: Wella Aktiengesellschaft, Darmstadt, Fed. Rep. of Germany

[21] Appl. No.: 749,535

[22] PCT Filed: Oct. 26, 1984

[86] PCT No.: PCT/EP84/00336

§ 371 Date: Jun. 20, 1985

§ 102(e) Date: Jun. 20, 1985

[87] PCT Pub. No.: WO85/02113

PCT Pub. Date: May 23, 1985

[30] Foreign Application Priority Data

Nov. 8, 1985 [DE] Fed. Rep. of Germany ....... 3340350

[51] Int. Cl.$^4$ .......................... A45D 7/00; A61K 7/06; A61K 7/08
[52] U.S. Cl. ........................................... 132/7; 8/406; 424/DIG. 4; 424/70
[58] Field of Search ............................... 424/70; 132/7

[56] References Cited

U.S. PATENT DOCUMENTS 3,098,795  7/1963  Kreps ..................................... 424/70
4,438,096  3/1984  Preston .................................. 424/70

FOREIGN PATENT DOCUMENTS 1555796  11/1979  United Kingdom ............... 514/847

Primary Examiner—Dale R. Ore
Attorney, Agent, or Firm—Michael J. Striker

[57] ABSTRACT

Hair treatment agent and process for hair treatment on the basis of an alcoholic solution containing a synergistic combination of (A) 0.1 to 40% by weight cetyl alcohol lactic ester and (B) 0.5 to 30% by weight of a monomer quaternary ammonium compound as well as 0 to 15% by weight water. The hair treatment agent may be diluted with water before use. It is applied to the still wet hair after the hair wash and is rinsed off with water after a reaction time of from 3 to 5 minutes. An excellent improvement of the combabillity, the touch and the luster of the hair is noticed with respect to hair treatments with the sole content of one of the two components (A) or (B).

10 Claims, No Drawings

HAIR TREATMENT AND PROCESS FOR HAIR TREATMENT

The subject matter of the invention relates to hair treatment agents, which contain cetyl alcohol lactic acid ester, hereinafter called cetyllactate, and at least one quaternary monomer ammonium compound in an alcoholic solution as well as hair treatment processes by using these hair treatment agents.

The hair structure is damaged by frequent bleaching, permanents and coloring, but also due to frequent washing with deoiling air entrainers and by intensive reaction to sunlight. The hair becomes brittle and it looses its luster. Furthermore, while combing the hair it is electrostatically charged and the roughened hair surface causes felting and knotting of the hair. This makes combing difficult. Therefore, hair treatment to improve combability has attained a considerable importance.

Hair treatment agents act for improving the hair condition and customarily are oil-in-water emulsions, which as a framework contain components of oily, semisolid or solid substances like, for example, paraffin oil, vaseline, wool fat, wool fat alcohols, fatty acid ester oils and hydrocarbon waxes. As emulsifiers for such emulsions customarily quaternary ammonium compounds are used, like oxethylized alkyl ammonium phosphates, alkyl trimethyl ammonium chlorides, dialkyl dimethyl ammonium chlorides, alkyl dimethyl benzyl ammonium chlorides and alkyl pyridinium chlorides alone or in combination with noniogenic emulsifiers. Also watery solutions and watery gels with a content of quaternary ammonium compounds are frequently used as a hair treatment agent. Such agents are frequently distributed on the hair in form of a clear hair care rinse, for example, or in form of an emulsion as a so-called creme rinse after the hair wash on the still wet hair, it will remain active on the hair for a few minutes and is then rinsed off with water.

The wet combability and the touch of the hair can be improved to a certain extent with hair treatment agents on the basis of monomer quaternary ammonium compounds.

In agents for the treatment of hair it is also known to use them as conditioners when the agents contain cationic active polymers, in particular polymers which contain quaternary ammonium groups. In view of an alternating reaction between their ammonium groups and the anionic groups of the hair the cationic active polymers have a great affinity with respect to the keratine fiber.

It had been found that the use of such cationic active polymers in such agents results in numerous advantages; the disentanglement of the hair as well as the treatment of which is facilitated, and in furtherance the hair gets bounceability and a luster. However, due to the affinity to the keratine the polymers tend to collect on the hair during frequent use, so that the hair becomes heavier which in the final analysis is undesireable.

As had been shown in practice in accordance with the state of the art these approaches are not fully satisfactory with respect to their hair conditioning effect, in particular concerning the touch, luster as well as the combability of the hair.

In contrast thereto, it now had been found that hair treatment agents in form of an ethanolic and/or isopropanolic solution with a content of a combination of (A) 1.0 to 40.0% by weight cetyl alcohol lactic acid ester and
(B) 0.5 to 30.0% by weight of a monomer quaternary ammonium compound as well as 0 to 15.0% by weight water have a surprising and excellent improvement of the wet and dry combability of the hair as well as an improved touch in particular of damaged hair. Moreover, an excellent luster of the hair is noticeable.

The excellent noticeable improvement of the combability, the luster and the touch is surprising and can only be synergistically explained, since cetyllactate or quaternary monomer ammonium compounds in a corresponding solution applied alone to the hair results merely in a moderate and insufficient improvement of the mentioned criteria. As tests have shown the combination of cetyllactate with quaternary polymers does not show the synergystic noticeable effect with respect to the described improvement of the combability, the luster and the touch of the hair, in contrast to the agents in accordance with the invention on the basis of cetyllactate and monomer quaternary ammonium compounds.

The hair treatment agents in accordance with the invention are applied in an amount of about 20 to 50 g, depending on the hair density, either in the form of the alcoholic solution after the hair is washed on the still wet hair or the agent is diluted with water before applying to the hair, whereby an alcoholic watery emulsion is generated which is then applied in the same manner. After a reaction time of about 3–5 minutes the hair is rinsed with water.

The described agents represent watery or slightly thickened alcoholic solutions which are characterized by a content of the synergistic combination of cetyllactate and a quaternary monomer ammonium compound in the amounts stated.

In the hair treatment agents in accordance with the invention, the cetyllactate should be present in an amount of 1 to 40% by weight, preferably in an amount of 8.0 to 20% by weight. The content of the quaternary monomer ammonium compound should be 0.5 to 30% by weight, preferably 1.5 to 10.0% by weight. The isopropyl alcohol or the ethanol or the mixture of these two alcohols should be present in the agents in an amount of from 30.0 to 98.5% by weight, preferably 60 to 95% by weight. Naturally, the hair treatment may contain in addition the customary cosmetic constituents and additives for hair treatment agents like, for example, perfume oils, aromatic extracts, bactericidal or fungicidal substances, denaturants, colorability color substances or dyes which can be directly applied to the hair.

As customary constituents of hair treatment agents water, acetone, n-propanol, cationic or noniogenic hair entrainers, oxethylized fatty alcohols, furthermore, natural modified natural or synthetic polymers, for example, chitosan; furthermore, thickeners, like fatty alcohols, fatty acid esters, cellulose derivatives, paraffins, isoparaffins, vaseline and wool wax as well as caring substances like lanolin derivatives, cholesterin and pantothene acid, antioxidants, preserving agents and antidandruf agents, for example, salicyclic acid, furthermore, pigments and dyes are being taken into consideration, for example.

Of the known cosmetic dyes, which may be present alone or in a mixture, the following classes may be mentioned by way of example: aromatic nitro dyes (for example, 1,4-diamino-2-nitrobenzene)azo dyes (for example, Acid Brown 4), anthraquinone dyes (for example, C.I. Disperse Violet 4) and triphenyl methane dyes (for example, Basic Violet 1), whereby the dyes of these classes have an acid, nonionogenic or basic character, depending on the type of its substituents. Their total concentration customarily is about 0.05 to 2.0% by weight.

If the hair treatment agent in accordance with the invention is diluted with water before being applied to the hair, one can customarily use tap water. However, the water used for dilution may be packaged separately for the inventive agent and may contain hair cosmetic substances like, for example, aromatic extracts, bactericidal or fungicidal substance, colorability dyes or dyes which can be applied to the hair, if this is advantageous.

The agents in accordance with the invention in form of alcoholic solutions may be diluted with water or the packaged watery solution to a ratio of up to 1:10, preferably at a ratio of 1:2 to 1:4.

The following examples shall explain the subject matter of the invention in more detail, without being limited thereto.

EXAMPLES

Example 1:

10 g cetyllactate
4 g distearyl dimethyl ammonium chloride, 75% (remainder:water)
86 g ethanol,pure (94.7% by weight)
100 g 15 test persons with strongly damaged hair were treated after a customary hair wash with 18 g each of a hair treatment agent in accordance with example 1. In order to obtain clear results and to eliminate deviating hair qualities from test person to test person, the hair was parted in the center and one half was treated with the preparation in accordance with the invention, while the other part remained untreated. In this manner, the effect of the preparation could be judged by a group of hairdresser experts. An evaluation was performed in accordance with the model for the compiled criteria wet and dry combability, touch and luster of the hair as follows:
1=very good
2=good
3=sufficient
4=insufficient
The result is shown in the following table 1.

|  | Grade 1 | Grade 2 | Grade 3 | Grade 4 |
|---|---|---|---|---|
| Number of the test persons | 12 | 2 | 1 | — |

Examining the Synergistic Effect

For examining the synergystic effect the hair of a further group of 12 persons were treated in the same manner as in example 1, however the hair treatment agent did not contain cetyllactate. In the compound in accordance with example 1, the cetyllactate was replaced by a further addition of 10 g ethanol. The result of the test is shown in the following table 2.

TABLE 2

|  | Grade 1 | Grade 2 | Grade 3 | Grade 4 |
|---|---|---|---|---|
| Number of the test persons | — | 2 | 9 | 1 |

For a further examination of the synergistic effect, a third group of people of 12 persons were treated in accordance with example 1, however, this time the hair treatment agent did not contain distearyl dimethyl ammonium chloride. In the compound in accordance with example 1, the distearyl dimethyl ammonium chloride had been replaced by the corresponding amount of ethanol. The result is shown in table 3.

TABLE 3

|  | Grade 1 | Grade 2 | Grade 2 | Grade 4 |
|---|---|---|---|---|
| Number of the test persons | — | — | 4 | 8 |

A comparison of the results of table 1, 2 and 3 clearly shows that the agent in accordance with the invention in accordance with example 1 has a synergistic effect in comparison to the corresponding agents with a content of only one each of the two components.

Example 2:
  5 g cetyllactate
  2 g cetyl trimethyl ammonium chloride, 25% watery solution
  1 g perfume oil
  92 g ethanol,pure (94.7% by weight)
  100 g Example 3:
  15 g cetyllactate
  3 g lauryl pyridinium chloride (90 to 94%)
  82 g ethanol,pure (94.7% by weight)
  100 g Example 4:
  12.0 g cetyllactate
  2.0 g tetradecyl trimethyl ammonium bromide
  0.1 g dye Basic Violet 1 (C.I.No.42 535)
  85.9 g ethanol,pure (94.7% by weight)
  100.0 g Example 5:
  20 g cetyllactate
  10 g tris (-oligooxyethyl) octadecyl ammonium phosphate
  70 g ethanol,pure (94.7% by weight)
  100 g Example 6:
  11.0 g cetyllactate
  6.0 g distearyl dimethyl ammonium chloride, 75% (remainder: water)
  0,1 g 2,4,4'-trichlor-2'-hydroxy diphenyl ether
  82.9 g ethanol,pure (94.7%)
  100.0 g Example 7:
  30 g cetyyllactate
  6 g methyl-tri ($C_8$–$C_{10}$—alkyl) ammonium chloride,855
  64 g ethanol,pure (94.7% by weight)
  100 g Example 8:
  19 g cetyllactate
  6 g distearyl dimethyl ammonium chloride, 75% (remainder: water)
  75 g isopropanol
  100 g 35 g of the hair treatment agent in accordance with examples 2 to 8 are distributed in the washed hair and again rinsed off with water after a reaction time of from 3 to 5 minutes. As a result, one obtains an excellent touch, luster as well as combability of the hair.

All percentage numbers stated in the application represent weight percent.

We claim:

1. A synergistic composition for treating hair for improving hair combability, luster and touch, which consists essentially of:
   (A) 1.0 to 40% by weight of cetyl alcohol lactic acid ester;
   (B) 0.5 to 30% by weight of a monoquaternary ammonium compound selected from the group consisting of distearyl dimethyl ammonium choride, lauryl pyridinium chloride, tetradecyl trimethyl ammonium bromide, tris-(oligooxyethyl)-octadecyl ammonium phosphate, methyltris($C_8$ to $C_{10}$ alkyl) ammonium chloride, and cetyl trimethyl ammonium chloride;
   (C) 30 to 98.5% by weight of ethanol, isopropanol, or mixtures thereof; and
   (D) 0 to 15% by weight water.

2. A synergistic composition for treating hair for improving hair combability, luster and touch, which consists essentially of:
   (A) 8 to 20% by weight of cetyl alcohol lactic acid ester;
   (B) 1.5 to 10% by weight of a monomer quaternary ammonium compound selected from the group consisting of distearyl dimethyl ammonium chloride, lauryl pyridinium chloride, tetradecyl trimethyl ammonium bromide, tris-(oligooxyethyl)-octadecyl ammonium phosphate, methyltris($C_8$ to $C_{10}$ alkyl) ammonium chloride, and cetyl trimethyl ammonium chloride;
   (C) 60 to 95% by weight of ethanol, isopropanol, or mixtures thereof; and
   (D) 0 to 15% by weight water.

3. The synergistic composition for treating hair defined in claim 2 wherein the monomer quaternary ammonium compound is distearyl dimethyl ammonium chloride.

4. The synergistic composition for treating hair defined in claim 2 which consists essentially of:
   (A) 10% by weight cetyl alcohol lactic acid ester;
   (B) 4% by weight of a 75% aqueous solution of distearyl dimethyl ammonium chloride; and
   (C) 86% by weight of ethyl alcohol.

5. A process for treating hair for improving hair combability, luster, and touch, which comprises the steps of:
   (1) wetting the hair;
   (2) applying to the hair wetted during step (1) 20 to 50 g of a synergistic, hair-treating composition consisting essentially of:
      (A) 1.0 to 40% by weight of cetyl alcohol lactic acid ester;
      (B) 0.5 to 30% by weight of a monoquaternary ammonium compound selected from the group consisting of distearyl dimethyl ammonium chloride, lauryl pyridinium chloride, tetradecyl trimethyl ammonium bromide, tris-(oligooxyethyl)-octadecyl ammonium phosphate, methyltris($C_8$ to $C_{10}$alkyl) ammonium chloride, and cetyl trimethyl ammonium chloride;
      (C) 30 to 98.5% by weight of ethanol, isopropanol, or mixtures thereof; and
      (D) 0 to 15% by weight water;
   (3) permitting the hair-treating composition to react with the hair for a period of 3 to 5 minutes; and
   (4) rinsing the hair.

6. The process for treating hair defined in claim 5 wherein prior to step (2) the synergistic hair-treating composition is diluted by a ratio of 1:2 to 1:4 with water or a watery solution.

7. The process for treating hair defined in claim 5 wherein prior to step (2) the synergistic hair treating composition is diluted by a ratio of 1:10 with water or a watery solution.

8. A process for treating hair for improving hair combability, luster, and touch, which comprises the steps of:
   (1) wetting the hair;
   (2) applying to the hair wetted during step (1) 20 to 50 g of a synergistic, hair-treating composition consisting essentially of:
      (A) 8 to 20% by weight of cetyl alcohol lactic acid ester;
      (B) 1.5 to 10% by weight of a monomer quaternary ammonium compound selected from the group consisting of distearyl dimethyl ammonium chloride, lauryl pyridinum chloride, tetradecyl trimethyl ammonium bromide, tris-(oligooxyethyl)-octadecyl ammonium phosphate, methyltris($C_8$ to $C_{10}$ alkyl) ammonium chloride, and cetyl trimethyl ammonium chloride;
      (C) 60 to 95% by weight of ethanol, isopropanol, or mixtures thereof; and
      (D) 0 to 15% by weight water.

9. The process for treating hair defined in claim 8 wherein according to step (2) the monoquaternary ammonium compound in the synergistic, hair-treating composition is distearyl dimethyl ammonium chloride.

10. The process for treating hair defined in claim 8 wherein according to step (2) the synergistic, hair-treating composition consists essentially of:
    (A) 10% by weight of cetyl alcohol lactic acid ester;
    (B) 4% by weight of a 75% aqueous solution of distearyl dimethyl ammonium chloride; and
    (C) 86% by weight of ethyl alcohol.

* * * * *

UNITED STATES PATENT AND TRADEMARK OFFICE
CERTIFICATE OF CORRECTION

PATENT NO. : 4 719 930

DATED : January 19, 1988

INVENTOR(S) : Paul Gross and Walter Keller

It is certified that error appears in the above-identified patent and that said Letters Patent is hereby corrected as shown below:

On the title page:

[30] The priority date should read:

-- November 8, 1983 --

Column 5, line 8 should read --sisting of distearyl dimethyl ammonium chloride--

Signed and Sealed this

Fifteenth Day of November, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4 719 930

DATED : January 19, 1988

INVENTOR(S) : Paul Gross and Walter Keller

It is certified that error appears in the above-identified patent and that said Letters Patent is hereby corrected as shown below:

Column 4, line 53 should read --chloride 85%--

Signed and Sealed this

Ninth Day of May, 1989

Attest:

DONALD J. QUIGG

*Attesting Officer*    *Commissioner of Patents and Trademarks*